(12) United States Patent
Warren

(10) Patent No.: US 9,642,924 B2
(45) Date of Patent: May 9, 2017

(54) CONTRAST AGENTS BASED ON LONG-LIVED NUCLEAR SINGLET STATES AND RELATED METHODS

(71) Applicant: Duke University, Durham, NC (US)

(72) Inventor: Warren S. Warren, Durham, NC (US)

(73) Assignee: Duke University, Durham, NC (US)

( * ) Notice: Subject to any disclaimer, the term of this patent is extended or adjusted under 35 U.S.C. 154(b) by 205 days.

(21) Appl. No.: 14/472,790

(22) Filed: Aug. 29, 2014

(65) Prior Publication Data

US 2015/0064113 A1 Mar. 5, 2015

Related U.S. Application Data

(60) Provisional application No. 61/871,457, filed on Aug. 29, 2013.

(51) Int. Cl.
A61B 5/055 (2006.01)
A61K 49/10 (2006.01)
A61K 49/06 (2006.01)

(52) U.S. Cl.
CPC ............. *A61K 49/10* (2013.01); *A61K 49/06* (2013.01)

(58) Field of Classification Search
None
See application file for complete search history.

(56) References Cited

U.S. PATENT DOCUMENTS

| | | | |
|---|---|---|---|
| 6,574,495 | B1 | 6/2003 | Golman et al. |
| 7,474,095 | B2 | 1/2009 | Levitt et al. |
| 8,980,225 | B2 | 3/2015 | Warren |
| 2007/0063700 | A1 | 3/2007 | Levitt et al. |
| 2008/0104966 | A1 | 5/2008 | Stautner |
| 2008/0260649 | A1 | 10/2008 | Thaning et al. |
| 2009/0060841 | A1 | 3/2009 | Yen et al. |
| 2011/0195028 | A1 | 8/2011 | Warren |
| 2012/0326717 | A1 | 12/2012 | Weitekamp et al. |
| 2013/0096420 | A1 | 4/2013 | Aime et al. |
| 2015/0258220 | A1 | 9/2015 | Warren |

FOREIGN PATENT DOCUMENTS

| | | | | |
|---|---|---|---|---|
| WO | WO99/35508 | * | 7/1999 | ............. G01R 33/28 |
| WO | WO2005/015253 | | 2/2005 | |
| WO | WO2010/014893 | | 2/2010 | |

OTHER PUBLICATIONS

Franzoni et al. (J. Am. Chem. Soc. 2012, 134, 10393-10396).*
Abragam, A., and Goldman, M., "Principles of dynamic nuclear polarisation," Rep. Prog. Phys. vol. 41 pp. 395-467 (1978).
Abraham, R.J., and Bernstein, H.J., "The Analysis of Nuclear Magnetic Resonance Spectra v. The Analysis of Deceptively Simple Spectra," Canadian Journal of Chemistry. vol. 39 pp. 216-230 (1961).
Ahuja et al., "Long-Lived States in Multiple-Spin Systems," ChemPhysChem., vol. 10, pp. 2217-2220 (2009).
Ahuja et al., "Molecular properties determined from the relaxation of long-lived spin states," The Journal of Chemical Physics. vol. 127 pp. 134112-1-134112-6 (2007).
Altes et al., "Hyperpolarized Gas MR Imaging of the Lung," J. Thorac. Imaging, vol. 19, pp. 250-258 (2004).
Anet, "Some Aspects of the Nuclear Magnetic Resonance Spectra of Compounds Containing C-Methyl Groups," Canadian Journal of Chemistry. vol. 39 pp. 2262-2273 (1961).
Ardenkjaer-Larsen et al., "Increase in signal-to-noise ratio of >10,000 times in liquid-state NMR," PNAS. vol. 100, No. 18 pp. 10158-10163 (2003).
Bajaj et al., "Dynamic nuclear polarization at 9T using a novel 250 GHz gyrotron microwave source," Journal of Magnetic Resonance vol. 160 pp. 85-90 (2003).
Becke, A.D., "Density-functional Thermochemistry. 3. The Role of Exact Exchange," J. Chem. Phys., vol. 98, pp. 5648-5652 (1993).
Becker, High Resolution NMR: Theory and Chemical Applications. Chapter 6. Academic, San Diego, CA pp. 171-175 (2000).
Bell, R.P., and McDougall, A.O., "Hydration Equilibria of Some Aldehydes and Ketones," Trans. Faraday Soc. vol. 56 pp. 1281-1285 (1960).
Bell, "The Reversible Hydration of Carbonyl Compounds," Adv. Phys. Org. Chem. vol. 4 pp. 1-29 (1966).
Bernstein et al., "The Analysis of Nuclear Magnetic Resonance Spectra. 1. Systems of 2 and 3 Nuclei," Can. J. Chem., vol. 35, pp. 65-81 (1957).
Bhattacharya et al., "Communication: Towards hyperpolarized 13C-succinate imaging of brain cancer," Journal of Magnetic Resonance. vol. 186 pp. 150-155 (2007).
Bloch et al., "Magnetic Resonance for Nonrotating Fields," Phys. Rev., vol. 57, pp. 522-527 (1940).
Bornet et al., "Boosting Dissolution Dynamic Nuclear Polarization by Cross Polarization," J. Phys. Chem. Lett., vol. 4, p. 111-114 (2013).
Bowers, C.R., and Weitekamp, D.P., "Transformations of Symmetrization Order to Nuclear-Spin Magnetization by Chemical Reaction and Nuclear Magnetic Resonance," Physical Review Letters. vol. 57, No. 21 pp. 2645-2648.
Bowers, C.R., and Weitkamp, D.P., "Parahydrogen and Synthesis Allow Dramatically Enhanced Nuclear Alignment," Journal American Chemical Society. vol. 109 pp. 5541-5542 (1987).
Brindle, et al., "Tumor Imaging Using Hyperpolarized (13)C Magnetic Resonance," Magn. Reson. Med., vol. 66, pp. 505-519 (2011).
Buljubasich et al., "Level Anti-Crossings in ParaHydrogen Induced Polarization Experiments with Cs-Symmetric Molecules," J. Magn. Reson., vol. 219, p. 33-40 (2012).

(Continued)

*Primary Examiner* — Michael G Hartley
*Assistant Examiner* — Melissa Perreira
(74) *Attorney, Agent, or Firm* — Jenkins, Wilson, Taylor & Hunt

(57) ABSTRACT

Methods are described for preparing magnetic resonance imaging (MRI) and/or magnetic resonance spectroscopy contrast agents where the contrast agents are prepared from precursor molecules having at least four non-zero-spin nuclei that form two pairs of chemically equivalent or effectively equivalent nuclei, e.g., diphenylacetylene or diethyl oxalate. The precursor molecule is hyperpolarized and a sequence of one or more radiofrequency pulses is applied to transfer spin state population between the first and second pair of nuclei, thereby providing a non-equilibrium single state nuclear spin population. To detect the contrast agent, another sequence of one or more radiofrequency pulses is applied to transfer singlet order to polarization. No transformation of the molecular structure of the contrast agent is necessary for detection. Also described are methods of imaging targets using the contrast agents.

15 Claims, 4 Drawing Sheets

(56) References Cited

OTHER PUBLICATIONS

Carravetta et al., "Beyond the T1 Limit: Singlet Nuclear Spin States in Low Magnetic Fields," Physical Review Letters. vol. 92, No. 15 pp. 153003-1-153003-4 (2004).
Carravetta M. and Levitt M.H., "Long-Lived Nuclear Spin States in High-Field Solution NMR," Journal American Chemical Society. vol. 126 pp. 6228-6229 (2004).
Carravetta M. and Levitt M.H., "Theory of long-lived nuclear spin states in solution nuclear magnetic resonance. I. Singlet states in low magnetic field," The Journal of Chemical Physics. vol. 122 pp. 214505-1-214505-14 (2005).
Chekmenev et al., "Pasadena Hyperpolarization of Succinic Acid fro MRI and NMR Spectroscopy," JACS. vol. 130 pp. 4212-4213 (2008).
Chen et al., Metabolism of (S)-5,6-Difluoro-4-CyclopropylethynylL-4-trifluoromethyl-3, 4-dihydro-2(1H)-quinazolinone, A Non-Nucleoside Reverse Transcriptase Inhibitor in Human Liver Microsomes. Metabolic Activation and Enzyme Kinetics, Drug Metab. Dispos, vol. 31, p. 122-132 (2003).
Chinchilla et al., "Recent Advances in Sonogashira Reactions," Chem. Soc. Rev., vol. 40, p. 5084-5121 (2011).
Davis et al., "Enthalpies of Hydrogenation of Phenylalkynes: Indirect Determination of Enthalpy of Formation of Diphenylcyclopropenone," J. Org. Chem., vol. 50, p. 360-3604 (1985).
Day et al., "Co-acquisition of hyperpolarised 13C and 15N NMR spectra," Magnetic Resonance in Chemistry. vol. 45 pp. 1018-1021 (2007).
de Boer, W., and Niinikoski T., "Dymanic Proton Polarization in Propanediol Below 0.5 K," Nuclear Instruments and Methods. vol. 114 pp. 495-498 (1974).
deBoer et al., "Dynamic Polarization of Protons, Deuterons, and Carbon-13 Nuclei: Thermal Contact Between Nuclear Spins and an Electron Spin-Spin Interaction Reservoir," Journal of Low Temperature Physics. vol. 15, Nos. 3/4 pp. 249-267 (1974).
Deng et al., "Calculation of Nuclear Spin-Spin Coupling Constants of Molecules with First and Second Row Atoms in Study of Basis Set Dependence," J. Chem. Theory Comput., vol. 2, pp. 1028-1037 (2006).
Duckett, S.B., and Sleigh, C.J., "Applications of the parahydrogen phenomenon: A chemical perspective," Progress in Nuclear Magnetic Resonance Spectroscopy. vol. 34, No. 1 pp. 71-92 (1999).
Feng et al., "Accessing long-lived nuclear sin let states between chemically equivalent spins without breaking symmetry," Nature Physics. vol. 8 pp. 831-837 (Sep. 16, 2012).
Feng et al., "Storage of hydrogen spin polarization in long-lived 13C2 singlet order and implications for hyperpolarized MRI," J. Am. Chem. Soc. vol. 135 pp. 9632-9635 (Jun. 20, 2013).
Franzoni et al., "Hyperpolarized 1H Long Lived States Originating From Parahydrogen Accessed by rf Irradiation," Phys. Chem. Chem. Phys. vol. 15 pp. 17233-17239 (Aug. 16, 2013).
Gabellieri et al., "Therapeutic Target Metabolism Observed Using Hyperpolarized 15N Choline," Journal American Chemical Society. vol. 130 pp. 4598-4599 (2008).
Golman et al., "Metobolic Imaging by Hyperpolarized 13C Magnetic Resonance Imaging for In vivo Tumor Diagnosis," Cancer Research. vol. 66, No. 22 pp. 10855-10860 (2006).
Golman et al., "Molecular imaging with endogenous substances," PNAS. vol. 100, No. 18 pp. 10435-10439 (2003).
Golman et al., "Parahydrogen-Induced Polarization in Imaging: Subsecond 13C Angiography," Magnetic Resonance in Medicine. vol. 46 pp. 1-5 (2001).
Golman et al., "Real-time Metabolic Imaging," Proc. Natl. Acad. Sci. USA, vol. 103, pp. 11270-11275 (2006).
Golman et al., "Silvanus Thompson Memorial Lecture Molecular Imaging Using Hyperpolarized C-13," Br. J. Radiol., vol. 76, pp. S118-S127 (2003).
Grant et al., "Long-lived States in Solution NMR: Theoretical Examples in Three- and Four-spin Systems," J. Magn. Reson., vol. 193, pp. 177-190 (2008).

Greenzaid et al., "A Nuclear Magnetic Resonance Study of the Reversible Hydration of Aliphatic Aldehydes and Ketones. I. Oxygen-17 and Proton Spectra and Equilibrium Constants," Journal of the American Chemical Society. vol. 89, No. 4 pp. 749-756 (1967).
Hall et al, "Polarization-Enhanced NMR Spectroscopy of Biomolecules in Frozen Solution," Science. vol. 276 pp. 930-932 (1997).
Hoecker, W.H., and Hammer, B.W., "Distribution of Diacetyl and Acetylmethylcarbinol Between Fat and Water, With Special Reference to Butter," J. Dairy Sci. vol. 25 pp. 175-185 (1942).
Hogben et al., "Multiple Decoherence-Free-States in Multi-Spin Systems," J. Magn. Reson., vol. 211, pp. 217-220 (2011).
Hoult et al., "A Signal-to-Noise Ratio of the Nuclear Magnetic Resonance Experiment," J. Mag. Reson. vol. 24, p. 71-85 (1976).
Jakobsen et al., "Safety of ultrasound contrast agents," Eur. Radiol. vol. 15 pp. 941-945 (2005).
Jannin et al., "High Field Dynamic Nuclear Polarization at 6.7 T: Carbon-13 Polarization Above 70% Within 20 Min.", Chem. Phys. Lett., vol. 549, p. 99-102 (2012).
Johansson et al., "Cerebral Perfusion Assessment by Bolus Tracking Using Hyperpolarized 13C," Magnetic Resonance in Medicine. vol. 51 pp. 464-472 (2004).
Jonischkeit et al., "Generating Long-Lasting 1H and 13C Hyperpolarization in Small Molecules with Parahydrogen-induced Polarization," J. Chem. Phys., vol. 124, 201109 (2006).
Kauczor et al., "MRI Using Hyperpolarized Noble Gases," Eur. Radiol., vol. 8, pp. 820-827 (1998).
Kiselyov et al., "4-(Azolylphenyl)-phthalazin-1-amines: Novel Inhibitors of VEGF Receptors I and II," Chemical Biol. Drug Des. vol. 68 pp. 308-313 (2006).
Kita et al., "Kinetics and Mechanism of Base Hydrolysis of Chromium (III) Complexes with Oxalates and Quinolinic Acid," Trans. Metal Chem., vol. 34, pp. 585-591 (2009).
Komaromi et al., "Efficient Copper-free Sonogashira Coupling of Aryl Chlorides with Palladium on Charcoal," Chem. Commun., p. 4968-4970 (2008).
Kuprov, I., "Diagonalization-free Implementation of Spin Relaxation Theory for Large Spin Systems," J. Magn. Reson., vol. 209, pp. 31-38 (2011).
Kuprov, I., "Polynomially Scaling Spin Dynamics II: Further State-Space Compression Using Krylov Subspace Techniques and Zero Track Elimination," J. Magn. Reson., vol. 195, pp. 45-51 (2008).
Kuprov, I., "Polynomially Scaling Spin Dynamics Simulation Algorithm Based on Adaptive State-Space Restriction," J. Magn. Reson., vol. 189, pp. 241-250 (2007).
Kurhanewicz et al., "Analysis of Cancer Metabolism by Imaging Hyperpolarized Nuclei: Prospects for Translation to Clinical Research," Neoplasia, vol. 13, pp. 81-97 (2011).
Kurhanewicz et al., "Current and Potential Applications of Clinical 13C MR Spectroscopy," The Journal of Nuclear Medicine. vol. 49, No. 3 pp. 341-344 (2008).
Leadbeater et al., "Rapid, Easy Copper-free Sonogashira Couplings Using Aryl Iodides and Activated Aryl Bromides," Tetrahedron Lett., vol. 44, p. 8653-8656 (2003).
Lee et al., "Species-Specific and Inhibitor-Independent Conformations of LpxC: Implications for Antiobiotic Design," Chem. Biol., vol. 18, p. 38-47 (2011).
Levitt, M.H., "Composite Pulses," Prog. Nucl. Magn. Reson. Spectrosc., vol. 18, pp. 61-122 (1986).
Liang et al., "Syntheses, Structures and Antibiotic Activities of LpxC Inhibitors Based on the Diacetylene Scaffold," J. Bioorg. Med. Chem., vol. 19, p. 852-860 (2011).
MacFall et al., "Human Lung Air Spaces: Potential for MR Imaging with Hyperpolarized He-3," Radiology. vol. 200, No. 2 pp. 553-558 (1996).
McCarney et al., "Hyperpolarized water as an authentic magnetic resonance imaging contrast agent," PNAS. vol. 104, No. 6 pp. 1754-1759 (2007).
McConnell et al., "Analysis of Spin-Spin Multiplets in Nuclear Magnetic Resonance Spectra," The Journal of Chemical Physics. vol. 23, No. 6 pp. 1152-1159 (1955).
McConnell et al., "Anisotropic Relaxation and Nuclear Magnetic Relaxation in Liquids," J. Chem. Phys., vol. 25, p. 1289 (1956).

(56) References Cited

OTHER PUBLICATIONS

Merritt et al., "Hyperpolarized 13C allows a direct measure of flux through a single enzyme-catalyzed step by NMR," PNAS. vol. 104, No. 50 pp. 19773-19777 (2007).
Mieville et al., "Scavenging Free Radicals to Preserve Enhancement and Extend Relaxation Times in NMR Using Dynamic Nuclear Polarization," Angew. Chem. Int. Ed., vol. 49, pp. 6182-6185 (2010).
Minucci et al., "Histone Deacetylase Inhibitors and the Promise of Epigenetic (and More) Treatments for Cancer," Nat. Rev. Cancer, vol. 6, p. 38-51 (2006).
Musher, J.I., and Corey, E.J., "Virtual Long-Range Spin-Spin Couplings in NMR," Tetrahedron. vol. 18 pp. 791-809 (1962).
Natterer, J., and Bargon, J., "Parahydroen induced polarization," Progress in Nuclear Magnetic Resonance Spectroscopy. vol. 31 pp. 293-315 (1997).
Notice of Allowance corresponding to U.S. Appl. No. 13/056,795 dated Oct. 24, 2014.
Notification Concerning Transmittal of the International Preliminary Report on Patentability (Chapter I of the Patent Cooperation Treaty) corresponding to International Patent Application No. PCT/US2009/052393 dated Feb. 10, 2011.
Notification of Transmittal of the International Search Report and the Written Opinion of the International Searching Authority, or the Declaration corresponding to International Patent Application No. PCT/US2009/052393 dated Apr. 23, 2010.
Official Action corresponding to U.S. Appl. No. 13/056,795 dated Dec. 10, 2012.
Official Action corresponding to U.S. Appl. No. 13/056,795 dated Feb. 26, 2014.
Olesen, O.V., and Linnet, K., "Hydroxylation and Demethylation of the Tricyclic Antidepressant Nortiptyline by cDNA-Expressed Human Cytochrome P-450 Isozymes," Drug Metabolism and Disposition. vol. 25, No. 6 pp. 740-744 (1997).
Oros et al., "Hyperpolarized Xenon in NMR and MRI," Phys, Med. Biol., vol. 49, pp. R105-R153 (2004).
Peralta et al., "Through-bond and Through-Space J(FF) Spin-spin Coupling in Peridifluoronaphthalenes: Accurate DFT Evaluation of the Four Contributions," J. Am. Chem. Soc., vol. 123, pp. 9162-9163 (2001).
Pileio et al., "Extremely Low-Frequency Spectroscopy in Low-Field Nuclear Magnetic Resonance," Phys. Rev. Lett., vol. 103, 083002 (2009).
Pileio et al., "J-Stabilization of singlet states in the solution NMR of multiple-spin systems," Journal of Magnetic Resonance. vol. 187, No. 1 pp. 141-145 (2007).
Pileio et al., "Long-lived Nuclear Singlet Order in Near-Equivalent 13C Spin Pairs," J. Am. Chem. Soc., vol. 134, pp. 17494-17497 (2012).
Pileio et al., "Long-Lived Nuclear Spin States in the Solution NMR of Four-Spin Systems," J. Magn. Reson., vol. 182, pp. 353-357 (2006).
Pileio et al., "Recycling and Imaging of Nuclear Singlet Hyperpolarization," J. Am. Chem. Soc., vol. 135, p. 5084-5088 (2013).
Pileio et al., "Relaxation Theory of Nuclear Singlet States in Two Spin-1/2 Systems," Prog. Nucl. Magn. Reson. Spectrosc., vol. 56, p. 217-231 (2010).
Pileio et al., "Storage of Nuclear Magnetization as Long-lived Singlet Order in Low Magnetic Field," Proc. Natl. Acad. Sci. USA. vol. 107 pp. 17135-17139 (2010).
Pileio et al., "The Long-Lived Nuclear Singlet State of 15N-nitrous oxide in Solution," J. Am. Chem. Soc., vol. 130, p. 12582-12583 (2008).
Pileio et al., "Theory of Long-Lived Nuclear Spin States in Solution Nuclear Magentic Resonance. II. Singlet Spin Locking," J. Chem. Phys., vol. 130, 214501 (2009).
Pople et al., "The Anaysis of Nuclear Magnetic Resonance Spectra. II. Two Pairs of Two Equivalent Nuclei," Canadian Journal of Chemistry. vol. 35 pp. 1060-1072 (1957).
Redfield, A.G., "On the Theory of Relaxation Processes," IBM J. Res. Dev., vol. 1, pp. 19-31 (1957).
Salerno et al., "Hyperpolarized noble gas MR imaging of the lung: Potential clinical applications," European Journal of Radiology. vol. 40 pp. 33-44 (2001).
Sarkar et al., "Singlet-State Exchange NMR Spectroscopy for the Study of Very Slow Dynamic Processes," J. Am. Chem. Soc., vol. 129, pp. 328-334 (2007).
Sletten et al., "From Mechanism to Mouse: A Tale of Two Bioorthogonal Reactions," Acc. Chem. Res., vol. 44, pp. 666-676 (2011).
Sychrovsky et al., "Nuclear Magnetic Resonance Spin-Spin Coupling Constants from Coupled Perturbed Density Functional Theory," J. Chem. Phys., vol. 113, pp. 3530-3547 (2000).
Tayler et al., "Paramagnetic Relaxation of Nuclear Singlet States," Phys. Chem. Chem. Phys. vol. 13 pp. 9128-9130 (2011).
Tayler et al., "Singlet Nuclear Magnetic Resonance of Nearly-Equivalent Spins," Phys. Chem. Chem. Phys. vol. 13 pp. 5556-5560 (2010).
Theis et al., "Composite and Shaped Pulses for Efficient and Robust Pumping of Disconnected Eigenstates in Magnetic Resonance," The Journal of Chemical Physics vol. 140, 014201 (2014.
van Rooy et al., "Bronchiolitis Obliterans Syndrome in Chemical Workers Producing Diacetyl for Food Flavorings," American Journal of Respiratory and Critical Care Medicine. vol. 176 pp. 498-504 (2007).
Vasos et al., "Long-lived States to Sustain Hyperpolarized Magnetization," Proc. Natl. Acad. Sci. USA, vol. 106, pp. 18469-18473 (2009).
Viale, A. and Aime, S., "Current Concepts on Hyperpolarized Molecules in MRI," Curr. Opin. Chem. Biol., vol. 14, pp. 90-96 (2010).
Vinogradov et al., "Long-lived States in Solution NMR: Selection Rules for Intramolecular Dipolar Relaxation in Low Magnetic Fields," J. Magn. Reson., vol. 188, 176-182 (2007).
Warren et al., "Increasing Hyperpolarized Spin Lifetimes Through True Singlet Eigenstates," Science. vol. 323 pp. 1711-1714 (2009).
Hogben et al. "Spinach—A Software Library for Simulation of Spin Dynamics in Large Spin Systems," J. Magnetic Resonance. vol. 208 pp. 179-194 (2011).

* cited by examiner

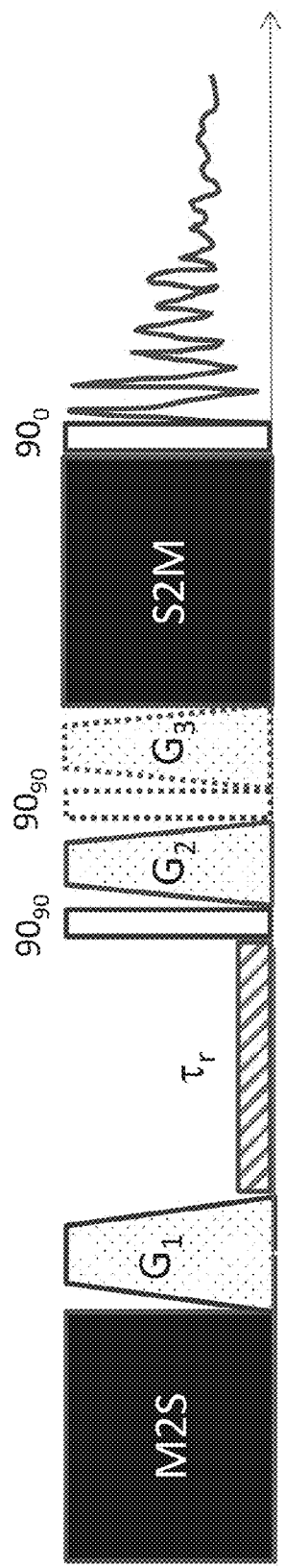
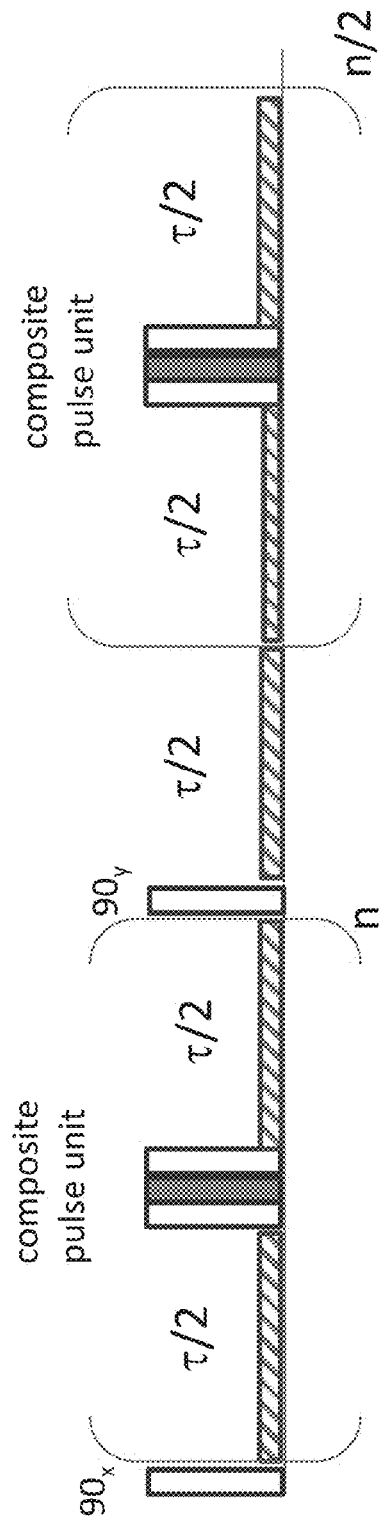
FIG. 1A
FIG. 1B

CONTRAST AGENTS BASED ON LONG-LIVED NUCLEAR SINGLET STATES AND RELATED METHODS

RELATED APPLICATIONS

The presently disclosed subject matter is based on and claims the benefit of U.S. Provisional Patent Application Ser. No. 61/871,457, filed Aug. 29, 2013; the disclosure of which is incorporated herein by reference in its entirety.

GOVERNMENT INTEREST

This invention was made with government support under Grant No. CHE-1058727 awarded by the National Science Foundation and Grant Nos. T32EB001040 and R01EB02122 awarded by National Institutes of Health. The government has certain rights in the invention.

TECHNICAL FIELD

The presently disclosed subject matter relates to methods of preparing magnetic resonance imaging and/or spectroscopy contrast agents having long-lived nuclear singlet states that can be accessed by pulse sequence transformation. Also provided are the contrast agents themselves and methods of using the contrast agents.

ABBREVIATIONS

°=degree
$^{13}$C=carbon-13
$^{13}$C-DEO=$^{13}$C$_2$-diethyl oxalate
$^{13}$C-DPA=$^{13}$C$_2$-1,2-diphenylacetylene
CW=continuous wave
DNP=dynamic nuclear polarization
Hz=hertz
M2S=magnetization-to-singlet
MRI=magnetic resonance imaging
ms=milliseconds
NMR=nuclear magnetic resonance
PET=positron emission tomography
RF=radiofrequency
s=seconds
S2M=singlet-to-magnetization
T=Tesla
$T_1$=longitudinal relaxation time constant
$T_2$=spin-spin relaxation time constant
$T_s$=singlet state lifetime

BACKGROUND

Nuclear magnetic resonance (NMR), or magnetic resonance spectroscopy, is a powerful, well-established tool for studying chemical samples and sample interactions. In NMR, the spin and magnetism of atomic nuclei are exploited to provide information about the chemical composition, spatial distribution, or molecular motion of molecules or atoms. The imaging analog of NMR, magnetic resonance imaging (MRI) is a powerful technique in biomedical sample imaging.

One of the limitations of NMR and MRI is low intrinsic signal strength. Some attempts to overcome this limitation have involved the use of hyperpolarized contrast agents, which have very large nuclear polarizations and, therefore, sensitivities that are orders of magnitude higher than ordinary molecules. Polarization can persist for as long as 100 seconds in some molecules before the polarized nuclei return to thermal equilibrium.

While such a lifetime is sufficient for some imaging and/or spectroscopy studies, contrast agents with longer lifetimes are highly desirable to study additional processes of interest, for example processes related to diffusion, flow, slow molecular motion, chemical reactions, metabolism, and drug targeting and distribution, among others. The relaxation of nuclear spins back to thermal equilibrium is characterized by a time constant, $T_1$, known as the longitudinal relaxation time constant or as the spin lattice relaxation time constant. The development of contrast agents having polarization that persists for times longer than $T_1$ would be beneficial for both NMR and MRI.

SUMMARY

In some embodiments, the presently disclosed subject matter provides a method of providing a contrast agent for magnetic resonance imaging (MRI) or magnetic resonance spectroscopy, the method comprising: providing a molecule comprising at least four non-zero-spin nuclei X, X', Y, and Y', wherein X and X' are a first pair of chemically equivalent or effectively equivalent nuclei, and Y and Y' are a second pair of chemically equivalent or effectively equivalent nuclei; hyperpolarizing the molecule to provide a hyperpolarized molecule; and applying a first sequence of one or more radiofrequency pulses to the hyperpolarized molecule to transfer a spin state population between the first and the second pair of chemically equivalent or effectively equivalent nuclei; thereby providing a contrast agent having a non-equilibrium singlet state nuclear spin population, wherein the contrast agent molecule can be detected after the application of a second sequence of one or more radiofrequency pulses to transfer singlet order to polarization.

In some embodiments, $J_{XX'}$, the scalar coupling between X and X', is greater than $J_{XY}$, the scalar coupling between X and Y; $J_{XY'}$, the scalar coupling between X and Y'; $J_{X'Y}$, the scalar coupling between X' and Y; and $J_{X'Y'}$, the scalar coupling between X' and Y'. In some embodiments, $J_{XX'}$ is at least three times greater than $J_{XY}$, $J_{XY'}$, $J_{X'Y}$, or $J_{X'Y'}$.

In some embodiments, the scalar coupling between X and X' is between about 10 and about 300 Hertz (Hz). In some embodiments, X and X' are both $^{13}$C or $^{15}$N nuclei. In some embodiments, the molecule has a molecular structure wherein X and X' are directly bonded to each other. In some embodiments, X and X' are free of directly bonded hydrogen atoms. In some embodiments, Y and Y' are both $^1$H or $^{19}$F nuclei.

In some embodiments, the molecule has a rigid molecular structure. In some embodiments, the molecule is selected from the group consisting of a diarylacetylene, diacetylene, an oxalate diester, a cyclooctyne or a lactone or lactam analog thereof, a dibenzocyclooctyne or a lactone or lactam analog thereof, a pyridazine, a phthalazine, and a gem-difluoro compound. In some embodiments, the molecule is selected from the group consisting of diphenylacetylene and diethyl oxalate. In some embodiments, the molecule has a symmetric molecular structure, X is chemically equivalent to X', and Y is chemically equivalent to Y'.

In some embodiments, the hyperpolarizing is performed by dynamic nuclear polarization (DNP). In some embodiments, the contrast agent can be provided and detected without undergoing a molecular structure transformation. In some embodiments, the contrast agent has a symmetrical molecular structure and can be detected without breaking the symmetry. In some embodiments, Y and Y' are $^1$H nuclei, and the one or more radiofrequency pulses are hydrogen-only pulse sequences.

In some embodiments, the contrast agent has pharmaceutical activity. In some embodiments, the contrast agent is formulated in a pharmaceutically acceptable carrier and administered to a subject. In some embodiments, the subject is a mammal.

In some embodiments, the non-equilibrium singlet state nuclear spin population can persist for a time that is greater than about 3 times the longitudinal relaxation time constant $T_1$. In some embodiments, the non-equilibrium singlet state nuclear spin population can persist for a time that is greater than about 10 times $T_1$. In some embodiments, the non-equilibrium singlet state nuclear spin population can persist for a time that is greater than about 50 times $T_1$. In some embodiments, the non-equilibrium singlet state nuclear spin population can persist for about 69 times $T_1$.

In some embodiments, the presently disclosed subject matter provides a method of imaging a target, the method comprising: providing a molecule comprising at least four non-zero-spin nuclei X, X', Y, and Y', wherein X and X' are a first pair of chemically equivalent or effectively equivalent nuclei, and Y and Y' are a second pair of chemically equivalent or effectively equivalent nuclei; hyperpolarizing the molecule to provide a hyperpolarized molecule; applying a first sequence of one or more radiofrequency pulses to the hyperpolarized molecule to transfer a spin state population between the first and second pair of nuclei, thereby providing a contrast agent having a non-equilibrium singlet state nuclear spin population; contacting the contrast agent with the target; applying a second sequence of one or more radiofrequency pulses to convert singlet order to magnetization; generating a nuclear magnetic resonance signal; and detecting the nuclear magnetic resonance signal, thereby imaging the target.

In some embodiments, the target is one of a cell, a tissue, an organ, and a subject. In some embodiments, the contacting comprises administering a pharmaceutical formulation comprising the contrast agent to a subject. In some embodiments, the subject is a mammal.

In some embodiments, the hyperpolarizing is performed by dynamic nuclear polarization (DNP).

In some embodiments, $J_{XX'}$, the scalar coupling between X and X', is greater than $J_{XY}$, the scalar coupling between X and Y; $J_{XY'}$, the scalar coupling between X and Y'; $J_{X'Y}$, the scalar coupling between X' and Y; and $J_{X'Y'}$, the scalar coupling between X' and Y'. In some embodiments, $J_{XX'}$ is at least three times greater than $J_{XY}$, $J_{XY'}$, $J_{X'Y}$, or $J_{X'Y'}$.

In some embodiments, the scalar coupling between X and X' is between about 10 and about 300 Hertz (Hz). In some embodiments, X and X' are both $^{13}$C or $^{15}$N nuclei. In some embodiments, the molecule has a molecular structure wherein X and X' are directly bonded to each other. In some embodiments, X and X' are free of directly bonded hydrogen atoms. In some embodiments, Y and Y' are both $^1$H or $^{19}$F nuclei.

In some embodiments, the molecule has a rigid molecular structure. In some embodiments, the molecule is selected from the group consisting of a diarylacetylene, diacetylene, an oxalate diester, a cyclooctyne or a lactone or lactam analog thereof, a dibenzocyclooctyne or a lactone or lactam analog thereof, a pyridazine, a phthalazine, and a gem-difluoro compound. In some embodiments, the molecule is selected from the group consisting of diphenylacetylene and diethyl oxalate. In some embodiments, the molecule has a symmetric molecular structure and X is chemically equivalent to X' and Y is chemically equivalent to Y'.

In some embodiments, the contrast agent can be detected without undergoing a molecular structure transformation. In some embodiments, the contrast agent has a symmetric molecular structure and can be detected without breaking the symmetry.

In some embodiments, Y and Y' are $^1$H nuclei, the one or more radiofrequency pulses of the first and second sequences are hydrogen-only pulse sequences; and the nuclear magnetic resonance signal is a hydrogen signal.

In some embodiments, the presently disclosed subject matter provides a contrast agent prepared by the method comprising: providing a molecule comprising at least four non-zero-spin nuclei X, X', Y, and Y', wherein X and X' are a first pair of chemically equivalent or effectively equivalent nuclei, and Y and Y' are a second pair of chemically equivalent or effectively equivalent nuclei; hyperpolarizing the molecule to provide a hyperpolarized molecule; and applying a first sequence of one or more radiofrequency pulses to the hyperpolarized molecule to transfer a spin state population between the first and the second pair of chemically equivalent or effectively equivalent nuclei; thereby providing a contrast agent having a non-equilibrium singlet state nuclear spin population, wherein the contrast agent molecule can be detected after the application of a second sequence of one or more radiofrequency pulses to transfer singlet order to polarization.

Accordingly, it is an object of the presently disclosed subject matter to provide methods of providing a contrast agent for magnetic resonance imaging (MRI) or magnetic resonance spectroscopy and to provide methods of imaging a target with a contrast agent.

An object of the presently disclosed subject matter having been stated hereinabove, and which is achieved in whole or in part by the presently disclosed subject matter, other objects will become evident as the description proceeds hereinbelow.

BRIEF DESCRIPTION OF THE DRAWINGS

FIG. 1A is a schematic drawing of pulse sequences according to an embodiment of the presently disclosed subject matter. The sequences include a magnetization-to-singlet (M2S) sequence to convert bulk magnetization to singlet order, followed by a singlet-to-magnetization sequence (S2M) to convert singlet order to bulk magnetization. After the S2M sequence, a 90° pulse is applied and magnetization is detected (zigzagging line at right). Between the M2S and S2M sequences, there is a first z-gradient, $G_1$, and a variable relaxation delay, $\tau_r$. The variable relaxation delay can be followed by at least one additional 90° pulse and one additional z-gradient, $G_2$. A third z-gradient ($G_3$) and the 90° pulse immediately prior to $G_3$ (both outlined in dotted lines) are optional. Signal acquisition is indicated by the squiggly line.

FIG. 1B is a schematic drawing showing additional details of the M2S sequence described for FIG. 1A. The M2S sequence includes a 90° pulse $90_x$ (shown as an unshaded rectangle) followed by a first multiple echo sequence (shown in brackets), which is repeated n times. The multiple echo sequence can include a delay ($\tau/2$, shown by the striped heavy line), a composite pulse unit (which includes a 90° pulse (unshaded rectangle), a 180° pulse (shaded rectangle), and another 90° pulse (unshaded rectangle)) and second $\tau/2$ delay (striped heavy line). Accordingly, between each composite pulse unit in the echo sequence is a delay of τ. Following the first multiple echo sequence is a 90° pulse $90_y$ (unshaded rectangle), another delay τ/2 (striped heavy line), and then a second multiple echo sequence (shown in the second set of brackets), which is the same as the first multiple echo sequence, only repeated half as many times (i.e., n/2).

DETAILED DESCRIPTION

Figure 2:
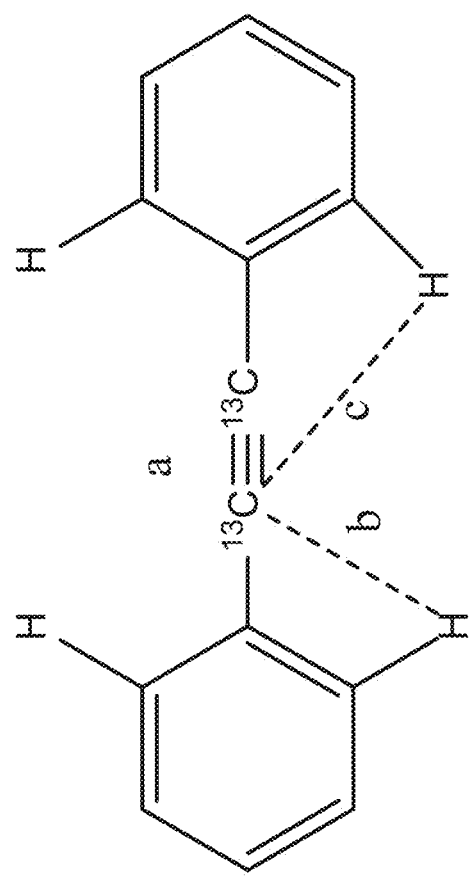
FIG. 2 is a drawing of the molecular structure of $^{13}C_2$-diphenylacetylene. The scalar coupling $^1J_{CC}$ (a) between the neighboring $^{13}C$ atoms is 182 Hz. The scalar coupling $^3J_{CH}$ (b) between the $^{13}C$ atom and the nearest aromatic hydrogen atom (i.e., the hydrogen three atoms away) is 5.5 Hz. The scalar coupling $^4J_{CH}$ (c) between the $^{13}C$ and the nearest aromatic hydrogen on the more distant phenyl ring (i.e., the hydrogen four atoms away) is −0.6 Hz.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist, unless otherwise noted.

I. DEFINITIONS

While the following terms are believed to be well understood by one of ordinary skill in the art, the following definitions are set forth to facilitate explanation of the presently disclosed subject matter.

Unless otherwise defined, all technical and scientific terms used herein have the same meaning as commonly understood by one of ordinary skill in the art to which this presently described subject matter belongs.

Following long-standing patent law convention, the terms "a", "an", and "the" refer to "one or more" when used in this application, including the claims. Thus, for example, reference to "a pharmaceutically acceptable carrier" includes mixtures of one or more carriers, two or more carriers, and the like.

The term "comprising", which is synonymous with "including," "containing," or "characterized by" is inclusive or open-ended and does not exclude additional, unrecited elements or method steps. "Comprising" is a term of art used in claim language, which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

The term "contrast agent" refers to a contrast agent molecule or a composition comprising a contrast agent molecule that increases the contrast of a tissue, organ, cell or other biological structure being examined, for example using nuclear magnetic resonance imaging (MRI). The contrast agent molecules of the presently disclosed subject matter can also be used to determine the progress of chemical reactions or non-biological phenomena (e.g., chemical diffusion) via nuclear magnetic resonance (NMR) spectroscopy.

The term "J-coupling" can also be referred to as spin-spin coupling or scalar coupling. As used herein, J-coupling can refer to a J coupling which is larger than the reciprocal of the spin-spin relaxation time, $T_2$.

As used herein the term "chemically equivalent nuclei" can refer to nuclei having the same chemical shift. Accordingly, molecules having chemically equivalent nuclei generally have a plane of symmetry, such that each of the two chemically equivalent nuclei are bonded to a chemical group or groups that have the same chemical structure or structures as the group or groups bonded to the other chemically equivalent nuclei. Non-chemically equivalent nuclei are generally bonded to one chemical group that is different in structure than the chemical group or groups bonded to the other non-chemically equivalent nuclei. Non-equivalent nuclei can have a resonance frequency difference which exceeds the J coupling between them.

The term "effectively equivalent nuclei" can refer to nuclei wherein, by coincidence or choice of field strength, the resonance frequencies of the nuclei will differ by less than the J coupling between them. For example, in some embodiments, the effectively equivalent nuclei can have a chemical shift difference that is at least three times (or, in some embodiments, at least five times) smaller than the J coupling between them.

The term "effectively equivalent nuclei" can, in some embodiments, refer to nuclei that are "nearly chemically equivalent" (or "nearly equivalent"), as well as to nuclei having a chemical shift difference that can be reduced or eliminated by radiofrequency pulses. The terms "nearly chemically equivalent" and "nearly equivalent" refer to nuclei that have a chemical shift difference that is smaller than the largest J coupling in the system (i.e., in the molecule). The methods described herein can be performed using a system having nearly equivalent nuclei as one or both of the nuclei pairs in the absence of any additional irradiation.

Non-zero-spin nuclei can be selected from the group including, but not limited to, $^1H$, $^2H$, $^{13}C$, $^{14}N$, $^{15}N$, $^{19}F$, and $^{31}$P. In some embodiments, providing the molecule comprising at least four non-zero-spin nuclei comprises synthetically doping or labeling a molecule with a particular isotope (e.g., with $^{13}$C).

The terms "sensitive" and "insensitive" as used herein with regard to nuclei can refer to the relative intensity of NMR signals of the nuclei. The signal intensity can relate to the gyromagnetic ratio ($\gamma$) of the nuclei, i.e., to the ratio of magnetic dipole moment to angular momentum. Generally, nuclei (e.g., $^{13}$C, $^{14}$N, $^{15}$N, etc.) with lower gyromagnetic ratios are more insensitive, while nuclei (e.g., $^{1}$H and $^{19}$F) with higher gyromagnetic ratios are more sensitive.

In some embodiments, hyperpolarizing is performed by dynamic nuclear polarization (DNP). DNP refers to transferring spin polarization from electrons to nuclei. In some embodiments, DNP can be performed by doping a material with a free radical. The unpaired electrons in the free radical can be polarized, for example, by exposure to a high magnetic field and low temperature. Irradiation at the electron paramagnetic resonance frequency can then serve to transfer polarization to the nuclei. However, the hyperpolarizing can be performed by other techniques known in the art, such as, but not limited to, reaction with para-hydrogen (i.e., by para-hydrogen induced polarization (PHIP)). By "hyperpolarization," it is meant that the sample is polarized to a level over that found at room temperature and 1 Tesla, for example, polarized to a polarization degree in excess of about 0.1%, in excess of about 1%, or in excess of about 10%.

The terms "molecular structure transformation" and "chemical transformation" can refer to chemical and biochemical reactions wherein one or more bonds are formed or broken.

The term "rigid structure" as used herein can refer to molecules having one or more bonds that do not have essentially free rotation. Such structures can include pi ($\pi$) bonds or bonding systems (e.g., a system of conjugated $\pi$ bonds) that are typically planar and/or substructures (e.g., ring structures) that have preferred conformations, for example, due to angle strain and/or torsional strain. In some embodiments, molecules with rigid molecular structure have one or more ring structures and/or a series of alternating single and multiple bonds (e.g., double or triple bonds).

In some embodiments, the target is one of a cell, a tissue, an organ, and a subject (e.g., a human or other mammal). In some embodiments, the contrast agent can be used in an NMR study and the target can be a chemical composition (e.g., a non-biochemical reaction mixture).

II. GENERAL CONSIDERATIONS

Nuclear magnetic resonance (NMR) and the imaging analog, magnetic resonance imaging (MRI), have become important techniques. MRI has become a powerful clinical imaging modality for two fundamental reasons. First, the hardware is mature: modern MRI machines routinely give complex sequences of arbitrarily shaped radiofrequency pulses to create precise excitation, and give magnetic field gradient pulses to suppress magnetization or obtain spatial resolution. More importantly, however, the theoretical framework is mature. No other modern spectroscopy has such a strong theoretical basis, which of course is used to understand the structures of molecules as complicated as proteins in solution. This maturity is even more important in MRI: complications associated with imaging in vivo can often be reduced or eliminated by clever pulse sequence design.

However, the maturity of that theoretical framework also implies that the known limitations of MRI are rather fundamental. The Boltzmann distribution implies that the net fractional magnetization is small at room temperature, so in most MRI studies, the signal arises mostly from water. Contrast then arises primarily from parameters that can be traced back to the spin physics explorations of the 1940s and 1950s (the local bulk magnetization $M_o$, the relaxation parameters $T_1$, $T_2$ and $T_2$*, and local values of diffusion, sometimes in different directions), which often only have very indirect clinical relevance or correlation with metabolism and cell biochemistry. MRI contrast agents generally have limited specificity, and usually need to be present in high concentration to affect the signal.

These limitations have recently been partially surmounted by the ready commercial availability of hyperpolarized reagents, which have very large nuclear polarizations and thus orders of magnitude higher sensitivity than ordinary molecules. Among the recent methods are techniques to create spin polarized $^3$He (see McFall et al., *Radiology*, 200, 553-558 (1996); and Salerno et al., *Eur. J. Radiol.*, 40, 33-44 (2001)), para-H$_2$ addition across double bonds (see Bowers and Weitekamp, *Phys. Rev. Lett.*, 57, 2645-2648 (1986); Bowers and Weitekamp, *J. Am. Chem. Soc.*, 109, 5541-5542 (1987); Natterer and Bargon, *Progr. Nucl., Magn. Res. Spectrosc.*, 31, 293-315 (1997); Duckett and Sleigh, *Progr. Magn. Res. Spectrosc.*, 34, 71-92 (1999); and Golman et al., *Magnetic Resonance in Medicine*, 46, 1-5 (2001)), and dynamic nuclear polarization (DNP). See Abragam and Goldman, *Rep. Prog., Phys.*, 41, 395-467 (1978); de Boer et al., *Journal of Low Temperature Physics*, 15, 249-267 (1974); de Boer and Niinikoski, *Nuclear Instruments and Methods*, 114, 495-498 (1974); Hall et al., *Science*, 276, 930-931 (1997); Bajaj et al., *Journal of Magnetic Resonance*, 160, 85-90 (2003); Johansson et al., *Magn. Reson. Med.*, 51, 464-472 (2004); and Ardenkjaer-Larsen et al., *Proc. Natl. Acad. Sci., USA*, 100, 10158-10163 (2003). All of these methods have demonstrated large nuclear magnetization (>10%, as compared to typical thermal magnetization of $10^{-5}$, with the polarization persisting as long as 100 s in some molecules. Many different research groups have been examining potential uses of such hyperpolarized molecules both in vivo and in vitro. See Kurhanewicz et al., *J. Nucl. Med.* 49(3), 341-344 (2008); Golman et al., *Cancer Research*, 66, 10855-10860 (2006); Merritt et al., *Proc. Natl. Acad. Sci., USA*, 104, 19773-19777 (2007); Day et al., *Mag. Res. Chem.*, 45(12), 1018-1021 (2007); Gabellieri et al., *J. Am. Chem. Soc.*, 130(14), 4598 (2008).

DNP methodology in particular is very versatile, and hundreds of different molecules have been polarized. However, most DNP studies have focused on $^{13}$C in pyruvate, largely because the $T_1$ relaxation time for the C1 position is relatively long (40 s at 14.1 T), so the polarized nuclei can potentially undergo many reactions before the NMR signal returns to thermal equilibrium and becomes undetectable. Generically, carbon-13 $T_1$ values are expected to be tens of seconds for carbons without attached protons, and much shorter with attached protons. While this lifetime permits some important metabolic processes to be studied, it is vastly shorter than the lifetimes associated with other molecular imaging modalities (e.g., $^{18}$F PET) and provides a fundamental limitation to the ultimate generality of the technique.

Previous studies have demonstrated the use of singlet states comprised of non-symmetry related spins to lengthen $T_1$. See Ahuja, et al., *J. Chemical Physics*, 127, 134112 (2007); Carravetta et al., *Physical Review Letters*, 92, 153003 (2004); Carravetta and Levitt, *J. Am. Chem. Soc.*, 126, 6228-6229 (2004); and Carravetta and Levitt, J. Chem. Physics, 122, 214505 (2005). In the studies, molecules with broken symmetry (for example, a single carbon-13) are used. The non-symmetry related spins are manipulated to appear to be equivalent by removing frequency differences with multiple spin echoes or by lowering the magnetic field so much that the resonance frequencies are essentially the same (which requires removing the sample from the magnet). The signal is then observed by permitting free evolution in a high field. Both approaches give interesting demonstrations of lifetime increases, but neither is practical for MRI. In addition, at the microscopic level, both of these approaches have certain limitations. For example, relaxation is dominated by the local components of the magnetic field fluctuating near the Larmor frequency, and, if two sites are physically inequivalent, these fluctuations are expected to be poorly correlated, even if the resonance frequencies are nearly the same.

PCT International Patent Application Publication No. WO 2005/015253 relates to an approach that involves lowering the field to create a pseudo-singlet state and to reacting an unsaturated symmetric molecule with parahydrogen to provide a quasi-equilibrium nuclear spin ensemble estate. See also, Carravetta et al. *Physical Review Letters*, 92, 153003 (2004); Carravetta and Levitt, *J. Am. Chem. Soc.*, 126, 6228-6229 (2004); and Carravetta and Levitt, J. Chem. Physics, 122, 214505 (2005).

PCT International Patent Application Publication No. WO 2010/014893 describes a method of imaging a target wherein a contrast agent is provided by preparing a compound having a non-equilibrium singlet state nuclear spin population wherein the singlet is between chemically equivalent spins. To detect the contrast agent, a chemical reaction is performed to break symmetry in the contrast agent. Thus, for example, the contrast agent can be provided by chemically converting a hyperpolarized molecule having two J-coupled, non-zero-spin, non-equivalent nuclei into a molecule wherein the previously non-equivalent nuclei are equivalent (e.g., by converting a non-symmetric molecule into a symmetric molecule). Then, magnetization stored in the contrast agent can be accessed by chemically converting the contrast agent into a detection molecule where the equivalent nuclei become non-equivalent again.

II.A. Accessing Singlet States Between Chemically Equivalent Spins without Breaking Symmetry According to the presently disclosed subject matter it is possible to transfer population in and out of chemically equivalent singlet states using only radiofrequency pulses. Thus, no molecular structure transformation of the contrast agent is required for detection (or formation). Accordingly, the presently disclosed methods can be performed without making, breaking or isomerizing any bonds in the contrast agent.

More particularly, the contrast agent of the presently disclosed subject matter can comprise at least two pairs of chemically equivalent or effectively equivalent non-zero-spin nuclei. According the presently disclosed methods, it is possible to create a coherence involving one pair of nuclei (e.g., carbon-13, nitrogen-14, nitrogen-15, deuterium (i.e., $^2$H), or some other relatively insensitive nuclei) and a second pair of nuclei (e.g., hydrogen or fluorine-19 or another more sensitive nuclei) that can be accessed completely through the sensitive nuclei, detected completely through the sensitive nuclei, or both, but has the longer lifetime associated with a singlet of the more insensitive nuclei.

More particularly, the presently disclosed subject matter is based on the ability to transfer population in and out of a singlet state at high field using only radiofrequency pulse sequences in molecular systems that comprise appropriate scalar couplings from the singlet spins to other spins in the molecule to break magnetic equivalence. An exemplary four-spin molecular system is $^{13}$C-diacetylene, i.e., H—C≡$^{13}$C—$^{13}$C≡C—H, where the $^{13}$C and H pairs are symmetric around the same center of inversion. The "singlet-singlet" state for this system, i.e., $|SS\rangle=|(\alpha\beta-\beta\alpha)_C(\alpha\beta-\beta\alpha)_H\rangle/2$, has no dipole-allowed transitions to other states, but does have the same overall inversion symmetry as the triplet-triplet state (i.e., $|T_0T_0\rangle=|(\alpha\beta+\beta\alpha)_C(\alpha\beta+\beta\alpha)_H\rangle/2$, which has dipole-allowed transitions. Thus, unlike the singlet state in a two-spin system, the singlet state in such a four-spin system is not isolated by symmetry from all other states. Accordingly, given appropriate scalar couplings, the "singlet-singlet" state of four-spin systems can essentially be an eigenstate. However, because this state has the same overall symmetry as the allowed triplet-triplet state, many different pulse sequences are capable of transferring population between them, such as the exemplary sequences described below. Additional theoretical considerations regarding four-spin molecular systems are described in Feng et al. (*Nature Physics*, 2012, 8, 831).

In some embodiments, the pulse sequences that can be used to migrate population between singlet and triplet states are similar to magnetization-to-w singlet-singlet-to-magnetization sequences (M2S-S2M) used to interconvert between slightly chemically equivalent spins (see Tayler and Levitt (*Phys. Chem. Chem. Phys.* 2011, 13, 5556); and Pileio et al. (*Proc. Natl. Acad. Sci. USA*, 2011, 107, 17135)), except that, according to the presently disclosed subject matter, chemical equivalence is preserved and magnetic equivalence is broken using scalar couplings. Thus, a train of 180° composite pulses separated by delays to allow accumulation of state mixing can interconvert the singlet and triplet states. As described in Example 1, below, interconversion between $^{13}$C magnetization and $^{13}$C$_2$-singlet order can be performed in the exemplary CC'H$_2$H$_2$' spin system in $^{13}$C$_2$-diethyl oxalate ($^{13}$C$_2$-DEO). Further, in some embodiments, the sequences can be selectively pulsed on either the insensitive nuclei (e.g., $^{13}$C) or the sensitive nuclei (e.g., $^1$H). Thus, as shown in Example 2, using the exemplary system of $^{13}$C$_2$-1,2-diphenylacetylene ($^{13}$C-DPA), $^1$H magnetization can be transferred into $^{13}$C$_2$ singlet polarization. Therefore, according to the presently disclosed subject matter, either $^{13}$C or $^1$H magnetization can be hyperpolarized and converted to $^{13}$C singlet polarization, which, for detection, can subsequently be converted back into either $^{13}$C or $^1$H magnetization.

FIG. 1A shows a M2S-S2M sequence that can be used according to the presently disclosed subject matter. The M2S sequence is separated from the S2M sequence by a z-gradient $G_1$, a relaxation delay $\tau_r$, and a combination of one or more additional z-gradients (e.g., $G_2$ and optional $G_3$ in FIG. 1A) and 90° pulses. The z-gradients and 90° pulses can eliminate residual triplet magnetization as well as any thermal magnetization that grows during the relaxation delay. In particular, the first z-gradient, $G_1$, can suppress single-quantum coherence generated by M2S. The 90° pulses have little effect on the polarization stored in the singlet state after the M2S sequence. After the S2M sequence (which can be a time-reversed M2S sequence), to convert single state population back to magnetization, a final 90° pulse provides for detection of the bulk magnetization.

The M2S sequence is shown in more detail in FIG. 1B. The M2S sequence includes a 90° pulse (i.e., $90_x$) followed by a first multiple echo sequence (first set of brackets). The multiple echo sequence can be equivalent to a Carr-Purcell-Meiboom-Gill (CPMG) sequence with each echo pulse composed of a $[90_0 180_{90} 90_0]\phi$ composite pulse unit, where $\phi$ is phase-cycled according to a composite pulse decoupling (CPD) scheme (i.e., MLEV4). The first multiple echo sequence is followed by a 90° pulse ($90_y$), which has a 90° phase shift compared to the first 90° pulse, $90_x$. A second multiple echo sequence (second set of brackets) follows an interpulse delay ($\tau/2$). The second multiple echo sequence has half as many pulses as the first multiple echo sequence.

The inter pulse delay and n are calculated based on the coupling constants of the particular molecule being used. For instance, in molecules wherein the more sensitive nuclei is $^1H$ and the less sensitive nuclei is $^{13}C$, $\tau$ can be calculated using the following formula:

$$\tau = 1/(2\sqrt{J^2_{CC}+(J_{CH}-J'_{CH})^2}).$$

In the exemplary molecule $^{13}C_2$-DPA, $J_{CC}$ is 182 HZ, $J_{CH}$=5.5 Hz, and $J'_{CH}$ is −0.6 Hz (see FIG. 2) providing $\tau$=1.365 ms. In the formula above, $J^2_{CC}$ can be replaced by $J_{CC}\pm(J_{HH})$, e.g., if $J_{HH}\neq 0$. The number of pulses n can be calculated using the formula:

$$n=\pi/(2\times\arctan((J_{CH}-J'_{CH})/J_{CC})).$$

For $^{13}$C-DPA, n=47.9. For practical purposes, this can be rounded up to 48. Similarly to the formula for $\tau$, if $J_{HH}\neq 0$, the term $J_{CC}$ can be replaced by $J_{CC}\pm(J_{HH})$.

In some embodiments, the relaxation delay, $\tau_r$, can be calculated using the formula:

$$\tau_r = 1/(2\sqrt{(J_{CC}\pm J_{HH})^2+(J_{CH}-J'_{CH})^2}.$$

In some embodiments, the presently disclosed subject matter provides a method of providing a contrast agent for magnetic resonance imaging (MRI) or magnetic resonance spectroscopy, the method comprising: providing a molecule comprising at least four non-zero-spin nuclei X, X', Y, and Y', wherein X and X' are a first pair of chemically equivalent or effectively equivalent nuclei, and Y and Y' are a second pair of chemically equivalent or effectively equivalent nuclei; hyperpolarizing the molecule to provide a hyperpolarized molecule; and applying a first sequence of one or more radiofrequency pulses to the hyperpolarized molecule to transfer a spin state population between the first and the second pair of chemically equivalent or effectively equivalent nuclei; thereby providing a contrast agent having a non-equilibrium singlet state nuclear spin population, wherein the contrast agent molecule can be detected after the application of a second sequence of one or more radiofrequency pulses to transfer singlet order to polarization.

The first sequence of one or more pulses is designed to put the molecule into a long-lived state. In a typical MRI application, the molecule can be injected into a subject at that point, and allowed to undergo various biochemical transformations, in some embodiments producing "metabolites." Thus, in useful applications, there can generally be a delay (e.g., a variable relaxation delay) between the first and second sequence of pulses. This delay can be many seconds or preferably many minutes. In order to see the signal, the second sequence of one or more radiofrequency pulses is applied to transfer singlet order back into an observable state.

In some embodiments, a metabolic reaction can change the molecular structure of the contrast agent to make chemically equivalent nuclei inequivalent, in which case, the long-lived state can be lost. Alternatively, in some embodiments, the metabolic reaction can change the molecular structure of the contrast agent, thereby changing resonance frequencies of some of the spins, in which case the metabolite can still have a long-lived state, but can be distinguishable from the original contrast agent molecule during detection. Accordingly, in some embodiments, "detection" of the contrast agent molecule refers to detection of a MRI or NMR signal of a molecule having the same molecular structure as the original molecule (i.e., the molecule with the four non-zero-spin nuclei). However, the contrast agent molecule can also be "detected" via detection of a MRI or NMR signal from a molecule that is a derivative of the original molecule, e.g., a metabolite formed when the contrast agent has undergone a biochemical transformation; or via the absence of an expected signal, e.g., when formation of a metabolite of the contrast agent molecule results in early loss of a long-lived singlet state.

In some embodiments, a pulsed field gradient (e.g., a z gradient) is applied to the contrast agent after the first sequence of one or more pulses is applied, but prior to the delay between the first and second sequences. In some embodiments, a pulsed field gradient (e.g., a z gradient) and a 90° pulse are applied to the contrast agent after the delay between the first and second sequence. In some embodiments, the post-delay pulsed field gradient and 90° pulse are repeated one or more times.

In some embodiments, the "effectively equivalent nuclei" can be "nearly equivalent" (e.g., having a chemical shift difference that is smaller than the largest J coupling in the molecule) or can have a chemical shift difference that can be reduced by radiofrequency pulses. In some embodiments, such as when the hyperpolarization provides large longitudinal order (e.g., when the hyperpolarization is by DNP), the first and second pulse sequences (e.g., M2S and S2M in FIG. 1a) can be the same sequence, simply reversed in time. Thus, in some embodiments, the same pulse sequence is used to convert conventional magnetization to the singlet and to convert from the singlet to conventional magnetization. In some embodiments, such as when hyperpolarization is by reaction with para-hydrogen, the first and second sequences can be different. For example, the M2S sequence can be shortened (or even completely omitted) compared to the S2M sequence when hyperpolarization is performed with para-hydrogen. However, in some embodiments, the first sequence includes at least one or more or at least two or more radiofrequency pulses.

Figure 3:
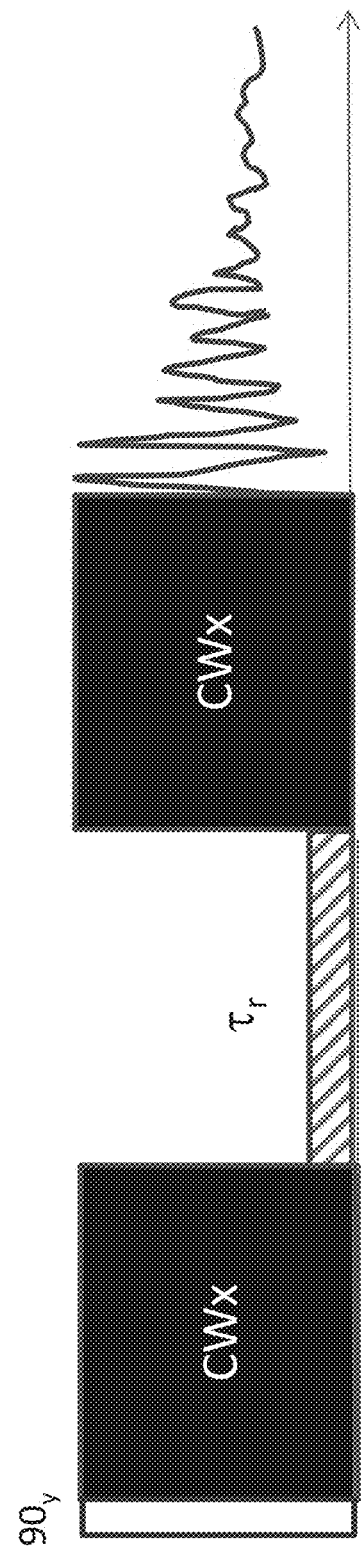
FIG. 3 is a schematic drawing of pulse sequences according to an alternative embodiment of the presently disclosed subject matter. The sequences include a 90 degree (90y) pulse followed by continuous wave irradiation (CWx) to transfer nuclear spin population into a long-lived singlet. After a variable relaxation delay (τr), a second continuous wave irradiation (CWx) is used to access the nuclear spin population. The amplitude (γB$_1$) of the continuous wave irradiations is matched to the largest in-pair J coupling (e.g., =2πJ$_{xx}$).

In some embodiments, e.g., to reduce energy dissipation, the M2S and S2M sequences can be replaced or modified using spin-lock induced crossing (SLIC) sequences that employ continuous wave (CW) irradiation. See Theis et al. (J. Chem. Phys. 2014, 140, 014201). Thus, in some embodiments (see FIG. 3), a 90° pulse (to create transverse magnetization) is followed by radiofrequency (RF) irradiation at a smaller amplitude to transfer nuclear spin population into a long-lived singlet. The RF irradiation (i.e., CWx in FIG. 3) can be 90° out of phase from the first pulse (i.e., along the direction of magnetization). The CW irradiation can be performed with a locking field based on $J_{XX'}$. Following a variable relaxation delay, an identical RF irradiation can be used to allow for detection of MRI or NMR signal.

Typically, X and X' are less sensitive than Y and Y'. In some embodiments, $J_{XX'}$, the scalar coupling between X and X' the less sensitive pair of chemically equivalent or effectively equivalent nuclei, is greater than $J_{XY}$, the scalar coupling between X and Y; $J_{XY'}$, the scalar coupling between X and Y'; $J_{X'Y}$, the scalar coupling between X' and Y; and $J_{X'Y'}$, the scalar coupling between X' and Y'. In some embodiments, $J_{XX'}$ is at least three times greater than $J_{XY}$, $J_{XY'}$, $J_{X'Y}$, or $J_{X'Y'}$. In some embodiments, $J_{XX'}$ can be less than three times greater than $J_{XY}$, $J_{XY'}$, $J_{X'Y}$, or $J_{X'Y'}$, such as when $J_{XY}$, $J_{XY'}$, $J_{X'Y}$, or $J_{X'Y'}$ can be reduced by applying radiofrequency pulses (e.g., only to Y and Y'). In some embodiments, the scalar coupling between X and X' is between about 10 and about 300 Hertz (Hz) (e.g., about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 Hz or a range involving any combination thereof).

In some embodiments, X and X' are both $^{13}C$ or $^{15}N$ nuclei. In some embodiments, X and X' are directly bonded to each other (e.g., via a nitrogen-nitrogen single bond, a carbon-carbon single bond, or by a carbon-carbon triple bond). In some embodiments, X and X' are free of directly bonded hydrogen atoms. In some embodiments, X and X' are nuclei with a spin >½ (e.g., $^{14}N$ or $^{2}H$). In some embodiments, Y and Y' are both $^{1}H$ or $^{19}F$ nuclei.

In some embodiments, there can be more than one pair of the more sensitive nuclei. For example, the contrast agent can be diphenylacetylene, wherein there are two carbons coupled to four chemically equivalent hydrogens and a long-lived carbon singlet can be populated from the hydrogens.

In some embodiments, the molecule has a rigid molecular structure. For example, the molecule can have a structure comprising one or more rings (i.e., one or more aromatic or non-aromatic ring structures) and/or one or more pi bonds (such as in an alkene or alkyne group). In some embodiments, the molecule is selected from the group comprising diarylacetylene, diacetylene, an oxalate diester, a cyclooctyne or a lactone or lactam analog thereof, a dibenzocyclooctyne or a lactone or lactam analog thereof, a pyridazine, a phthalazine, and a gem-difluoro compound. By "lactone or lactam analog thereof" is mean that two carbon atoms in the cyclooctyne ring are replaced by —C(=O)—O— or —C(=O)—NH—. In some embodiments, the molecule has a symmetric molecular structure. In some embodiments, X is chemically equivalent to X' and Y is chemically equivalent to Y'. Thus, in some embodiments, the contrast agent has a symmetrical molecular structure and can be detected without breaking the symmetry. In some embodiments, the molecule is selected from the group comprising diphenylacetylene and diethyl oxalate (e.g., $^{13}C$ labelled diphenylacetylene or diethyl oxalate).

Molecular structures of exemplary molecules that can be used as contrast agents according to the presently disclosed subject matter are shown in Table 1, below. The $^{13}C$ and $^{15}N$ atoms are indicated by * markings. Also included in Table 1 are estimated $T_s/T_1$ ratios, which are calculated at magnetic fields ($B_0$) of 8.45 T or 3 T (unless otherwise indicated) and ratios of scalar couplings.

TABLE 1

Exemplary Molecules with Isolated $^{13}C$ or $^{15}N$ Spin Pairs and Suitable Scalar Couplings.

| Structure | $T_s/T_1$ ($B_0$ = 8.45 T) | $T_s/T_1$ ($B_0$ = 3 T) | $J_{CC(NN)}/J_{CH(NH)}$ $J_{NN}/\Delta\omega$ |
|---|---|---|---|
| 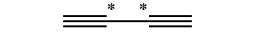 | 4.8 | 14.5 | 3.8 |
| 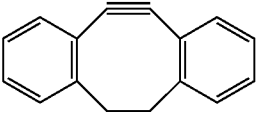 | 3.6 | 8.9 | 28 |
| 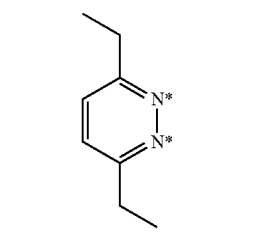 | 7.2 | 9.1 | 6 |
| 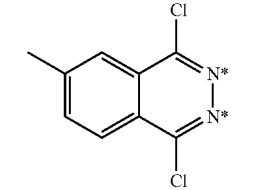 | — | 12 | 4.3 |
| 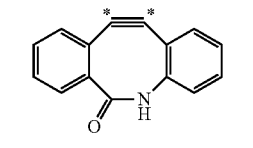 [SMILES: O=C1Nc2ccccc2C#Cc2ccccc21] | — | 16† | 5.4, 29† |
| 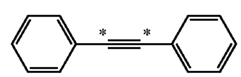 | 22.9 | 33.1 | |
| 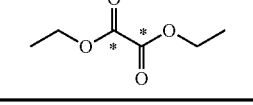 | 6.4 | 29.9 | |

Time constants in are derived from the inverse of matrix elements of the incoherent relaxation superoperator. Relaxation due to coherent oscillation is disregarded because it is quenched by dominant scalar couplings across the singlet spin pair. **The two $^{15}N$ spins have an estimated chemical shift difference $\Delta\omega$ of 3 ppm. The $T_s/T_1$ ratio is estimated at a field strength of 0.5 T, leading to a $J_{NN}/\Delta\omega$ ratio around 4.3.
†A chemical shift difference of about 2 ppm is estimated between the $^{13}C_2$ spin pair. Estimations of lifetime extension are made at field strength of 1.5 T, where $J_{CC}/J_{CH} \cong 29$ and $J_{CC}/\Delta\omega \cong 5.4$.

In some embodiments, Y and Y' are $^{1}H$ nuclei, and the one or more radiofrequency pulses (e.g., of the first and/or second sequences) are hydrogen-only pulse sequences. Thus, in some embodiments, $^{1}H$ magnetization can be converted into $^{13}C_2$-singlet or $^{15}N_2$-singlet polarization and then converted back into $^{1}H$ magnetization for detection. Accordingly, in some embodiments, the presently disclosed contrast agents and methods can be used with NMR and MRI equipment that does not possess heteronuclear capabilities, e.g., with standard clinical MRI imagers). The signals of the aromatic protons of many of the presently disclosed contrast agents can be readily distinguished from noise due to water and/or fat.

In some embodiments, the contrast agent has pharmaceutical activity. For instance, the molecule having the at least four non-zero-spin nuclei X, X', Y, and Y' can be a modified version of a molecule with a known pharmaceutical activity. In some embodiments, the molecule with known pharmaceutical activity can be modified by being labeled or doped with a suitable isotope (e.g., $^{13}C$ or $^{15}N$). In some embodiments, the molecule with known pharmaceutical activity can be modified by being conjugated (covalently or non-covalently) to a system having at least four non-zero-spin nuclei. For instance, derivatives of $^{13}C_2$-DPA can be prepared, e.g., with aromatic substituents having functional groups that can be used to conjugate the $^{13}C_2$-DPA to another molecule that has biological activity, without significantly disturbing the spin system of the $^{13}C_2$-DPA. Examples of pharmaceutically active molecules that can be modified to include a suitable system having at least four non-zero-spin nuclei include, but are not limited to, various antibiotics, e.g., the UDP-(3-O—(R-3-hydroxymyristoyl))-N-acetylglucosamine deacetylase (LpxC) inhibitor CHIR-090, and anticancer drugs, e.g., suberolyanilide hydroxamic acid (SAHA), also known as Vorinostat. The structures of CHIR-090 and SAHA are shown below in Scheme 1.

Scheme 1. Structures of Pharmaceuticals than Can be Modified for Use in the Presently Disclosed Methods.

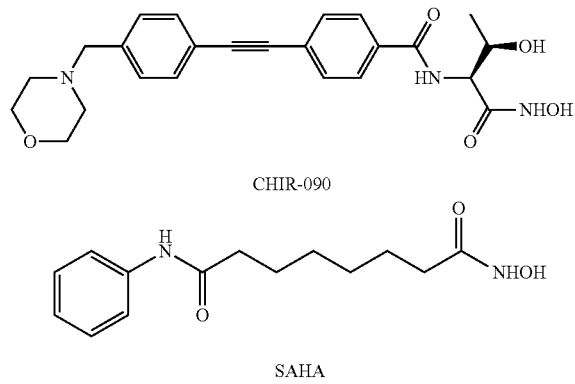

CHIR-090

SAHA

In some embodiments, the contrast agent is formulated in a pharmaceutically acceptable carrier and administered to a subject, such as a human or other mammal. In some embodiments, the term "pharmaceutically acceptable carrier" refers to a carrier that is pharmaceutically acceptable in humans, including water, saline and aqueous solutions that can comprise other diluents in addition to water, including, but not limited to, ethanol, propylene glycol, glycerin, and the like.

In some embodiments, the contrast agent molecule can be encapsulated into a delivery format or vehicle to protect the contrast agent molecule from one or more conditions in an in vivo environment or to aid in delivery of the contrast agent molecule to a specific location in a subject (e.g., to a particular organ or to tumor). Thus, the delivery format can include one or more targeting groups (e.g., an antibody, antigen, receptor ligand, enzyme substrate, or the like).

In some embodiments, the non-equilibrium singlet state nuclear spin population can persist for a time that is greater than about 3 times $T_1$, greater than about 5 times $T_1$, greater than about 10 times $T_1$, greater than about 20 times $T_1$, greater than about 30 times $T_1$, greater than about 40 times $T_1$, or greater than about 50 times $T_1$. In some embodiments, the non-equilibrium singlet state nuclear spin population can persist for about 69 times $T_1$.

II.B. Imaging Methods

The presently disclosed subject matter provides, in some embodiments, a method of imaging a target. In some embodiments, the method comprises: providing a molecule comprising at least four non-zero-spin nuclei X, X', Y, and Y', wherein X and X' are a first pair of chemically equivalent or effectively equivalent nuclei, and Y and Y' are a second pair of chemically equivalent or effectively equivalent nuclei; hyperpolarizing the molecule to provide a hyperpolarized molecule; applying a first sequence of one or more radiofrequency pulses to the hyperpolarized molecule to transfer a spin state population between the first and second pair of nuclei, thereby providing a contrast agent having a non-equilibrium singlet state nuclear spin population; contacting the contrast agent with the target; applying a second sequence of one or more radiofrequency pulses (e.g., to the contrast agent or to the target) to convert singlet order to magnetization; generating a nuclear magnetic resonance signal; and detecting a nuclear magnetic resonance signal, thereby imaging the target.

The target can be selected from the group comprising a cell, a tissue, an organ, and a subject (e.g., a human or other mammal). Thus, in some embodiments, the contacting comprises administering a pharmaceutical formulation comprising the contrast agent to a subject or administering an encapsulated and/or targeted contrast agent to a subject. Thus, in some embodiments, such as when the contrast agent is for use in an in vivo MRI study, the method can further comprise incorporating the contrast agent molecule into a pharmaceutically acceptable carrier or delivery vehicle to provide a pharmaceutically acceptable formulation suitable for administration to a subject.

In some embodiments, the subject is a mammal. In some embodiments, the mammal is a human; however, the presently disclosed subject matter also relates to the administration of contrast agents to any mammal (e.g., dogs, cats, horses, cows, goats, sheep, and the like, including both animals kept on farms and in zoos). Thus, the presently disclosed MRI contrast agents can be used in both medical and veterinary practice.

The formulation can include stabilizers, antioxidants, osmolality adjusting agents, solubilizing agents, emulsifiers, viscosity enhancers, buffers, etc. The formulation can be in forms suitable for parenteral (e.g., intravenous or intraarterial) or enteral (e.g., oral or rectal) application, for example for application directly into body cavities or for injection or infusion into the cardiovascular system. The formulation can be free of paramagnetic, superparamagnetic, ferromagnetic, and/or ferromagnetic contaminants. In some embodiments, the administration is parenteral, e.g., via bolus injection, by intravenous or intra-arterial injection, or, if the lungs are to be imaged, by spray, e.g., via aerosol spray.

For use in in vivo imaging, the formulation can be isotonic or slightly hypertonic and/or can be administered at a concentration sufficient to yield a 1 micromolar to 1 M concentration of the MR contrast agent in the imaging zone. Precise concentration and dosage can vary depending upon, for example, toxicity, the organ targeting ability of the contrast agent or its delivery vehicle, the tissue or organ being imaged, and the administration route. In general, any suitable concentration that yields a detectable signal can be used. In some embodiments, the concentration can be between about 0.1 mM and about 10 M, e.g., between about 0.2 mM and 1 M or between about 0.5 mM and about 500 mM. Formulations for intravenous or intraarterial administration can be between about 10 mM to 10 M, e.g., between about 50 mM and about 500 mM. For bolus injections, the concentration can be between about 0.1 mM and about 10 M, e.g., between about 0.2 mM and about 10 M, between about 0.5 mM and about 1 M, between about 1.0 mM and about 500 mM, or between about 10 mM and about 300 mM. Suitable aqueous carriers can include, but are not limited to, sodium chloride solution, Ringer's solution, dextrose solution, dextrose and sodium chloride solution, lactated Ringer's solution, etc.

The contrast agent/molecule with four non-zero-spin nuclei can have a structure as described hereinabove in Section II.A. In some embodiments, the contrast agent has pharmaceutical activity or is conjugated to a molecule with pharmaceutical activity. Thus, in some embodiments, the imaging can provide information regarding drug delivery. In some embodiments, the contrast agent can target particular biomolecules. For example, the contrast agent can be a cyclooctyne derivative, such as one of the cyclooctyne derivatives in Table 1, above. Such molecules can undergo a strain-promoted azide-alkyne reaction and can be used for labeling of particular biomolecules. Thus, in some embodiments, a cyclooctyne derivative can be used according to the presently disclosed methods as an in vivo molecular imaging agent. In some embodiments, the signal from the contrast agent can vary (e.g., the chemical shift can vary) in response to physiological conditions (e.g., pH, temperature, metabolism, calcium concentration, oxygen tension, etc.). Information about the physiological conditions detected with the contrast agent can provide information about disease state. For example, pH can be used as a general disease marker, while metabolic information detected using the contrast agents can be used to detect cancer.

In some embodiments, the contrast agent can be used in an NMR study and the target can be a chemical composition (e.g., a non-biochemical reaction mixture or an environmental sample, such as a water sample from a lake, stream, river, ocean, residential water supply, or industrial site). Therefore, in some embodiments, the contacting comprises mixing a contrast agent into an ex vivo sample, such as a reaction aliquot or environmental sample. In some embodiments, the contrast agent can be dissolved in a suitable solvent prior to the mixing.

Figure 4:
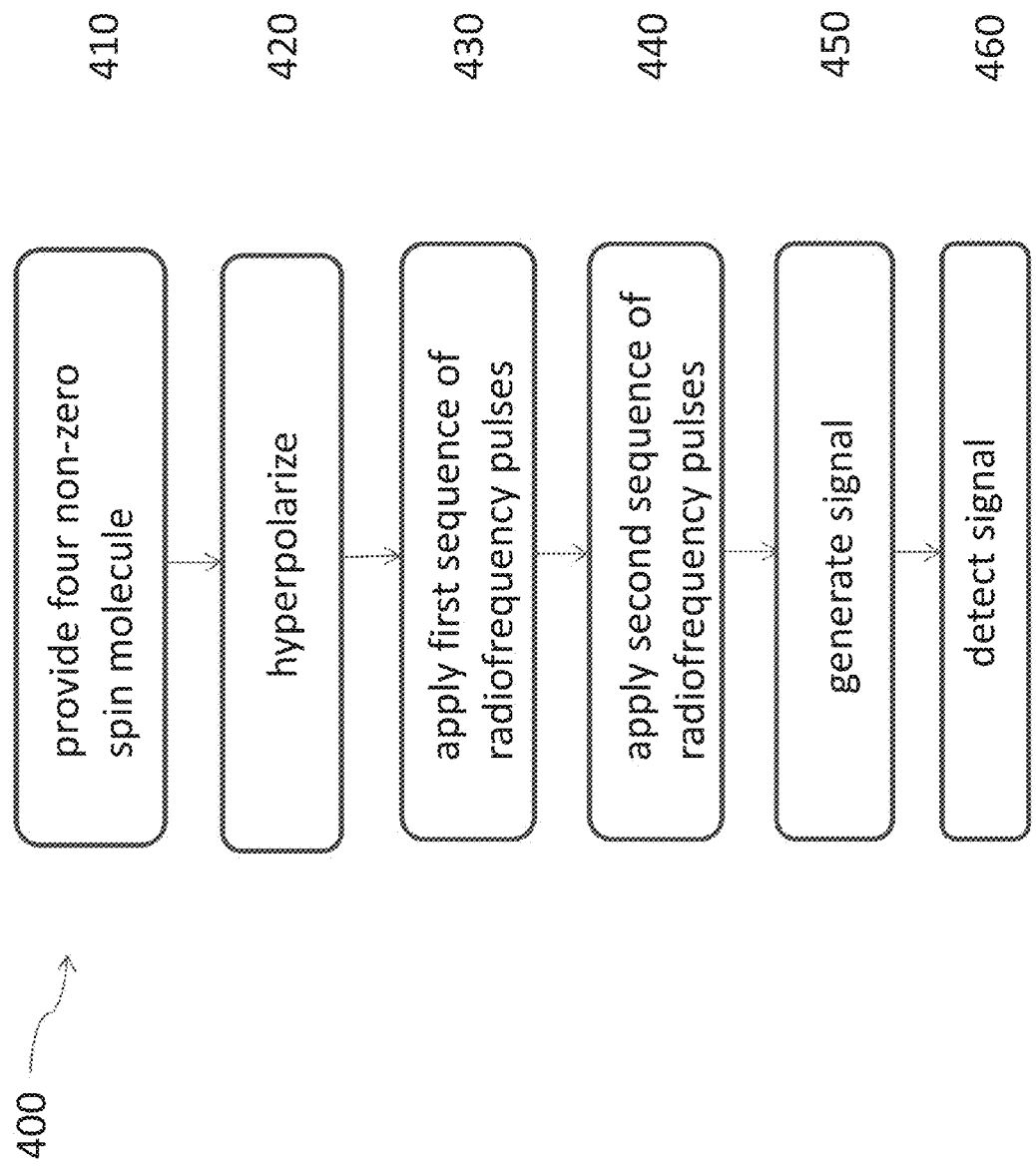
FIG. 4 is a schematic drawing showing a flow diagram of an imaging method according to one embodiment of the presently disclosed subject matter.

FIG. 4 shows a schematic diagram of an imaging method 400 of the presently disclosed subject matter. As shown in FIG. 4, in step 410, a suitable molecule can be provided, e.g., a molecule with at least four non-zero-spin nuclei, wherein the at least four non-zero-spin nuclei include a first pair of chemically equivalent or effectively equivalent nuclei and a second pair of chemically equivalent or effectively equivalent nuclei. The providing can include labelling, doping and/or conjugating the molecule to another molecule (e.g., a molecule with pharmaceutical activity). The molecule can have a structure as described above in Section II.A (e.g., have suitable scalar couplings and/or a rigid structure). In step 420, the molecule is hyperpolarized, e.g., via DNP.

So that the molecule remains sufficiently polarized, the molecule can be contacted with (e.g., administered to) the target as soon as possible. Thus, in some embodiments, step 420 is performed in close proximity to NMR or MRI equipment. Alternatively, the hyperpolarized molecule can be stored and/or transported to the target at low temperature (e.g., in liquid nitrogen). Prior to administration to a subject, the hyperpolarized molecule can be warmed to physiological temperatures, e.g., using infrared or microwave radiation.

After contact with the target, the remaining steps, i.e., step 430, application of a first sequence of one or more radiofrequency pulses (e.g., to convert magnetization of singlet order); step 440, application of a second sequence of one or more radiofrequency pulses (e.g., to convert singlet order to magnetization), step 450, generation of a NMR or MRI signal; and step 460, detection of the signal, can be performed.

In other embodiments, magnetization can be converted to singlet order at the site of hyperpolarization (e.g., within the hyperpolarizer) to avoid loss of magnetization. Therefore, in some embodiments, the molecule can be contacted to a target after step 430, but before steps 440, 450, and 460.

In some embodiments, the first and/or second sequences are hydrogen-only pulse sequences and the signal being generated or detected is a hydrogen signal. Thus, in some embodiments, the method can be performed in a conventional clinical MR imager without heteronuclear capability.

In some embodiments, the presently disclosed subject matter provides a contrast agent, prepared according to the methods disclosed herein, wherein the contrast agent can be used to enhance a signal in one of magnetic resonance imaging or magnetic resonance spectroscopy.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

$^{13}C_2$-Diethyl Oxylate

Studies with $^{13}C_2$-diethyl oxylate (DEO) were performed. Briefly, for thermal polarization spectra, $^{13}C_2$-DEO (Isotec Inc., Miamisburg, Ohio, United States of America) was dissolved in undegassed dimethyl sulfoxide (DMSO)-$d_6$ at a 2 M concentration and spectra were acquired on a Bruker 360 MHz (~8.45 T) magnet (Bruker Biosciences Corporation, Billerica, Mass., United States of America) with a 5 mm $^1$H and X broadband probe. Hyperpolarized spectra were acquired on a 7 T Bruker Biospect small animal MRI scanner (Bruker Biosciences Corporation, Billerica, Mass., United States of America) using samples containing 4 µl $^{13}C_2$-DEO (Isotec Inc., Miamisburg, Ohio, United States of America) 1 µl DMSO (Sigma-Aldrich, St. Louis, Mo., United States of America) and 15 mM Finland Radical (GE Healthcare, Little Chalfont, United Kingdom). Hyperpolarization was performed using a Hypersense hyperpolarizer (Oxford Instruments Molecular Biotools, Enysham, United Kingdom), after which the sample was dissolved in 3 ml additional DMSO at 140° C. to provide a solution of 0.8 mM hyperpolarized DEO. The liquid state polarization of the hyperpolarized DEO, 40 s after dissolution was measured to be 3,300 times greater than thermal polarization.

To determine the relaxation rate of the singlet state, a line was least-squares fitted to a plot of $\ln(S_{hyperpolarized,\ singlet}/S_{Thermal})$ as a function of $\tau_r$. $S_{hyperpolarized,\ singlet}/S_{Thermal}$ was determined from the equation: $S_{hyperpolarized,\ singlet}/$ $S_{Thermal}=3,300\times(\sin(5°)/\sin(90°))\times(S(MSM)/S(5°\text{-acquire}))$ where S(MSM) is the signal after the M2S-S2M sequence and S(5°-acquire) is the signal of a 5°-acquire pulse sequence performed 100 ms before the M2S-S2M sequence.

Simulated spectra $^{13}C_2$-DEO were provided by initial prediction of chemical structure and nuclear parameters (e.g., chemical shielding, scalar couplings, etc.) by density functional theory (DFT) methods using Gaussian 09 (Gaussian, Inc., Wallingford, Conn., United States of America). The SPINACH software library for simulation of spin dynamics (see Hogben et al., *J. Magn. Reson.*, 2011, 208, 179) was then used to simulate the effect of the M2S-S2M sequence and predict the relaxation profile of the compound based on the predicted parameters assuming a 40 picosecond rotational correlation time.

For $^{13}C_2$-DEO, $J_{CC}=101.6$ Hz and $J_{CH}=3.4$ Hz (e.g., between each carbon and the adjacent methylene proton). Interconversion between the triplet and singlet of $^{13}C_2$-DEO was manifested in the $^{13}C$ NMR spectra by an inversion of the two middle side peaks of the pentet signal. An interpulse delay τ of 4.92 ms induced the most efficient exchange between the carbon singlet and triplet manifolds in both the experimental and simulated spectra. Also, in both experimental and simulated spectra, the maximum conversion appeared after 45 echo pulses of the initial part of the M2S sequence (i.e., n=45, n/2=22). Signal decay after the complete M2S-S2M sequence showed slow singlet order decay after an initial fast triplet signal decay both experimentally and via simulation. Based on the experimental data, $T_s$ is around 50.6 s and $T_1$ around 22.2 s. Based on the simulation data, $T_s$ is about 110.2 s and $T_1$ about 17 s. Without being bound to any one theory, these differences are believed to be due to the dipole-dipole interactions with remote methyl protons that were disregarded in the simulation and the lack of degassing of the solvent.

Example 2

$^{13}C_2$-DPA 1,3-Diphenyl-$^{13}C_2$-ethyne ($^{13}C_2$-DPA) was prepared. Briefly, $^{13}C_2$-ethynylbenzene was combined with iodobenzene (1.05 eq) in the presence of $PdCl_2(PPh_3)_2$ (0.02 eq.) and piperidine (3 eq.) under an inert atmosphere and heated to 70° C. The reaction mixture was stirred at 70° C. for 10 minutes, and then the resulting semi-solid was diluted with 20 ml of water and extracted with ethyl acetate. The organic layers were washed with 1 N HCL, water, and brine and dried over anhydrous sodium sulfate. After evaporation of the solvent, the crude product was purified by chromatography (elution with hexanes) to provide 80 mg (89% yield) of white solid 1,3-diphenyl-$^{13}C_2$-ethyne.

For NMR studies, the M2S-S2M sequence of FIG. 1A, including three z-gradients $G_1$, $G_2$, and $G_3$, was used. More particularly, for $^{13}C_2$-DPA studies, $G_1=3$ ms, $G_2=4.5$ ms, and $G_3=11$ ms. The z-gradients have odd relationships to avoid gradient refocused echoes. Using the formulae described hereinabove for n and τ and the above-noted J couplings for $^{13}C_2$-DPA, n was calculated as 47.9 and as 1.365 ms. Experimentally, these values were adjusted to n=48 and τ=1.38 ms (which includes 40 μs for the composite pulses). For some studies, proton decoupling was performed with continuous wave irradiation using a decoupling power of $v_{RF}=0.5$ Hz.

The normal one-dimensional $^{13}C$ NMR spectra of $^{13}C_2$-DPA provided the expected pentet centered at 89.4 ppm. After the sequence of FIG. 1A is applied (with a 20 s delay $τ_r$ between M2S and S2M) where all of the pulses are applied at the $^{13}C$ Larmor frequency, the spectra shows a doublet, as only the magnetization detected as the doublet is perturbed by the sequence and stored as singlet polarization. When the sequence of FIG. 1A is performed with the pulses in the M2S applied at the $^{1}H$ Larmor frequency and the remaining pulses in the $^{13}C$ Larmor frequency, the spectra is also a doublet; however, the signal intensity is about 4 times larger than when all of the pulses are applied at the $^{13}C$ Larmor frequency. Without being bound to any one theory, this is believed to be due to the higher initial $^{1}H$ polarization compared to the initial $^{13}C$ polarization. That the signal is also a doublet confirms that the source of the signal is $^{13}C_2$ singlet order.

Using simulations performed in a manner similar to those for $^{13}C_2$-DEO, $T_s$ was predicted to be 274.7±6.1 s and no difference was predicted when $^{1}H$ decoupling was implemented. Using an isotropic rotational correlation time of 25 ps, $T_1$ was 12 s at 8.45 T. The experimentally observed $^{13}C_2$-DPA singlet state relaxation time at 8.45 T was 288.4±3.7 s without $^{1}H$ decoupling and 267.1±5.4 s with decoupling between the M2S and S2M. Since n and τ are independent of field strength, spectra and stimulations were repeated at different field strengths. Table 2 shows simulated (i.e., theoretical) and experimental $T_s$ and $T_1$ at various field strengths. Detection occurs on the S2M channel (i.e., for an experiment type that has S2M($^{1}H$), detection involves proton signal).

TABLE 2

Theoretical and Experimental $T_1$ and $T_s$ of $^{13}C_{12}$-DPA.

| Field Strength ($B_0$ (T)) | Experiment Type | Theoretical $T_1$ ($^{13}C$) | Theoretical $T_s$ | Experimental $T_1$ ($^{13}C$; $^{1}H$) | Experimental $T_s$ |
|---|---|---|---|---|---|
| 8.45 | M2S($^{13}C$), S2M($^{13}C$) | 12.2 s | 274.7 ± 6.1 | $^{13}C$, 13.9 s; $^{1}H$, 3.7 s | 288.4 ± 3.7 |
| 8.45 | M2S($^{13}C$), S2M($^{13}C$), with $^{1}H$ decoupling | — | 274.7 ± 6.1 | — | 267.1 ± 5.4 |
| 8.45 | M2S($^{1}H$), S2M($^{13}C$) | — | 273.2 ± 7.5 | — | 282.7 ± 3.8 |
| 16.44 | M2S($^{13}C$), S2M($^{13}C$) | 4.6 s | 252.0 ± 5.0 | $^{13}C$, 4.9 s; $^{1}H$, 3.8 s | 244.7 ± 1.4 |
| 16.44 | M2S($^{13}C$), S2M($^{1}H$) | — | 276.7 ± 8.5 | — | 223 ± 9.1 |

TABLE 2-continued

Theoretical and Experimental $T_1$ and $T_s$ of $^{13}C_{12}$-DPA.

| Field Strength ($B_0$ (T)) | Experiment Type | Theoretical $T_1$ ($^{13}C$) | Theoretical $T_s$ | Experimental $T_1$ ($^{13}C$; $^1H$) | Experimental $T_s$ |
|---|---|---|---|---|---|
| 16.44 | M2S($^1H$), S2M($^1H$) | — | 252.5 ± 15.3 | — | 261.7 ± 7.3 |
| 1.5 | M2S($^{13}C$), S2M($^{13}C$) | 29.1 s | 309.3 ± 8.2 | — | |

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of providing a contrast agent for magnetic resonance imaging (MRI) or magnetic resonance spectroscopy, the method comprising:
providing a molecule comprising at least four non-zero-spin nuclei X, X', Y, and Y', wherein X and X' are a first pair of chemically equivalent or effectively equivalent nuclei, and Y and Y' are a second pair of chemically equivalent or effectively equivalent nuclei, wherein the molecule is selected from the group consisting of diphenylacetylene and diethyl oxalate;
hyperpolarizing the molecule to provide a hyperpolarized molecule; and
applying a first sequence of one or more radiofrequency pulses to the hyperpolarized molecule to transfer a spin state population between the first and the second pair of chemically equivalent or effectively equivalent nuclei; thereby providing a contrast agent having a non-equilibrium singlet state nuclear spin population, wherein the contrast agent molecule can be detected after the application of a second sequence of one or more radiofrequency pulses to transfer singlet order to polarization.

2. The method of claim 1, wherein the hyperpolarizing is performed by dynamic nuclear polarization (DNP).

3. The method of claim 1, wherein the one or more radiofrequency pulses are hydrogen-only pulse sequences.

4. The method of claim 1, further wherein the contrast agent is formulated in a pharmaceutically acceptable carrier and administered to a subject.

5. The method of claim 4, wherein the subject is a mammal.

6. The method of claim 1, wherein the non-equilibrium singlet state nuclear spin population can persist for a time that is greater than about 3 times the longitudinal relaxation time constant ($T_1$).

7. The method of claim 6, wherein the non-equilibrium singlet state nuclear spin population can persist for a time that is greater than about 10 times $T_1$.

8. The method of claim 7, wherein the non-equilibrium singlet state nuclear spin population can persist for a time that is greater than about 50 times $T_1$.

9. A method of imaging a target, the method comprising:
providing a molecule comprising at least four non-zero-spin nuclei X, X', Y, and Y', wherein X and X' are a first pair of chemically equivalent or effectively equivalent nuclei, and Y and Y' are a second pair of chemically equivalent or effectively equivalent nuclei, wherein the molecule is selected from the group consisting of diphenylacetylene and diethyl oxalate;
hyperpolarizing the molecule to provide a hyperpolarized molecule;
applying a first sequence of one or more radiofrequency pulses to the hyperpolarized molecule to transfer a spin state population between the first and second pair of nuclei, thereby providing a contrast agent having a non-equilibrium singlet state nuclear spin population;
contacting the contrast agent with the target;
applying a second sequence of one or more radiofrequency pulses to convert singlet order to magnetization;
generating a nuclear magnetic resonance signal; and
detecting the nuclear magnetic resonance signal, thereby imaging the target.

10. The method of claim 9, wherein the target is one of a cell, a tissue, an organ, and a subject.

11. The method of claim 9, wherein the contacting comprises administering a pharmaceutical formulation comprising the contrast agent to a subject.

12. The method of claim 11, wherein the subject is a mammal.

13. The method of claim 9, wherein the hyperpolarizing is performed by dynamic nuclear polarization (DNP).

14. The method of claim 8, wherein the non-equilibrium singlet state nuclear spin population can persist for about 69 times $T_1$.

15. The method of claim 9, wherein the one or more radiofrequency pulses of the first and second sequences are hydrogen-only pulse sequences; and wherein the nuclear magnetic resonance signal is a hydrogen signal.

* * * * *